Figure 4:
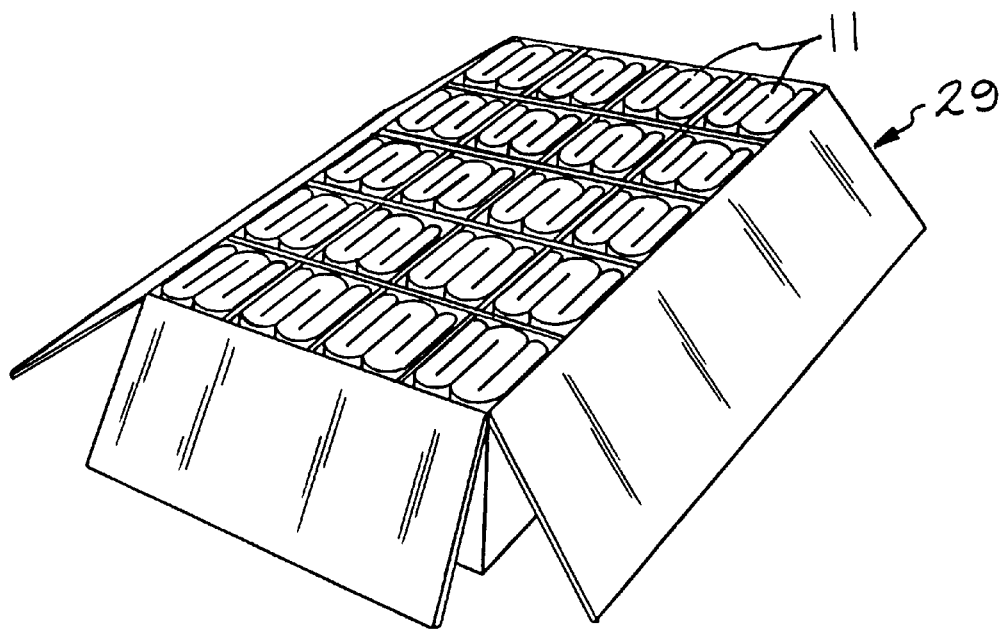

United States Patent [19]
Glendening et al.

[11] Patent Number: 5,935,843
[45] Date of Patent: *Aug. 10, 1999

[54] METHOD AND APPARATUS FOR WASTE DEGRADATION

[75] Inventors: Larrick H. Glendening, Bradenton; Vincent J. Scuilla, Sarasota, both of Fla.

[73] Assignee: Osprey Biotechnics, Inc., Oneco, Fla.

[ * ] Notice: This patent issued on a continued prosecution application filed under 37 CFR 1.53(d), and is subject to the twenty year patent term provisions of 35 U.S.C. 154(a)(2).

[21] Appl. No.: 07/834,771

[22] Filed: Feb. 13, 1992

[51] Int. Cl.⁶ ............................... C12S 9/00; C12S 13/00
[52] U.S. Cl. .......................... 435/262; 435/264; 210/606
[58] Field of Search .................... 435/243, 260, 435/262, 264, 284, 288, 289, 296, 810, 290, 316; 210/606, 610, 611, 614, 632, 737, 87, 88, 89, 138, 139, 141, 198.1; 137/240; 134/57 R, 95, 169 R; 222/92, 105, 107; 53/281, 390; 206/525, 526; 211/76, 84; 383/906

[56] References Cited

U.S. PATENT DOCUMENTS

| | | |
|---|---|---|
| 4,058,213 | 11/1977 | Stone . |
| 4,138,036 | 2/1979 | Bond ........................ 222/105 |
| 4,205,132 | 5/1980 | Sandine et al. ............. 435/260 |
| 4,229,544 | 10/1980 | Haynes et al. ............. 435/260 |
| 4,415,085 | 11/1983 | Clarke et al. .............. 222/107 |
| 4,452,894 | 6/1984 | Olsen et al. ............... 435/253 |
| 4,593,003 | 6/1986 | Vandenbergh ........... 435/172.3 |
| 4,786,192 | 11/1988 | Graves et al. . |
| 4,879,239 | 11/1989 | Daggett et al. ........... 435/260 |
| 4,910,143 | 3/1990 | Vandenbergh ......... 435/252.34 |
| 4,911,832 | 3/1990 | Miller et al. .............. 435/262 |
| 4,994,391 | 2/1991 | Hoffmann . |

FOREIGN PATENT DOCUMENTS

| | | |
|---|---|---|
| 0071365 | 2/1983 | European Pat. Off. . |
| 2158458 | 11/1985 | United Kingdom .......... 435/287 |
| 9002167 | 3/1990 | WIPO ......................... 435/287 |

OTHER PUBLICATIONS

Abstract, WPI Acc#83–15356k/07, WILDE, European Patent No. 71365 (Feb. 9, 1983).
Vandenbergh, P.A. and A.M. Wright, Appl. Environ. Microbiol. 45: 1953–1955 (1983).
Vandenbergh, P.A., C.F. Gonzales, A. M. Wright and B.S. Kunka, Appl. Environ. Microbiol 46:128–132 (1983).
Vandenbergh, P.A., R.H. Olsen and J.R. Colaruotolo, Appl. Environ, Microbiol. 42: 737–739 (1981).
Vandenbergh, P.A., and R.L. Cole, Appl. Environ. Microbiol. 52: 939–940 (1986).

*Primary Examiner*—William H. Beisner
*Attorney, Agent, or Firm*—Ian C. McLeod

[57] ABSTRACT

A liquid waste degradation apparatus (10) and method using microorganism (15) in solution (13) to degrade waste compositions typically found in restaurant settings, is described. The microorganisms are initially cultivated and concentrated to between about $10^9$ and $10^{12}$ cells per gram, preferably dried and then placed in bags (11) for shipment to end users. To activate the microorganisms, the bags containing the microorganisms are provided in a support container and filled with water. The resulting solution is then periodically dispersed into a waste trap (21) holding the liquid waste composition by means of a peristaltic pump (25) controlled by a timer (27) so that the microorganisms can feed on the waste material to degrade the waste material. A waste degradation system (100) particularly adapted for use in an industrial setting is also described.

23 Claims, 3 Drawing Sheets

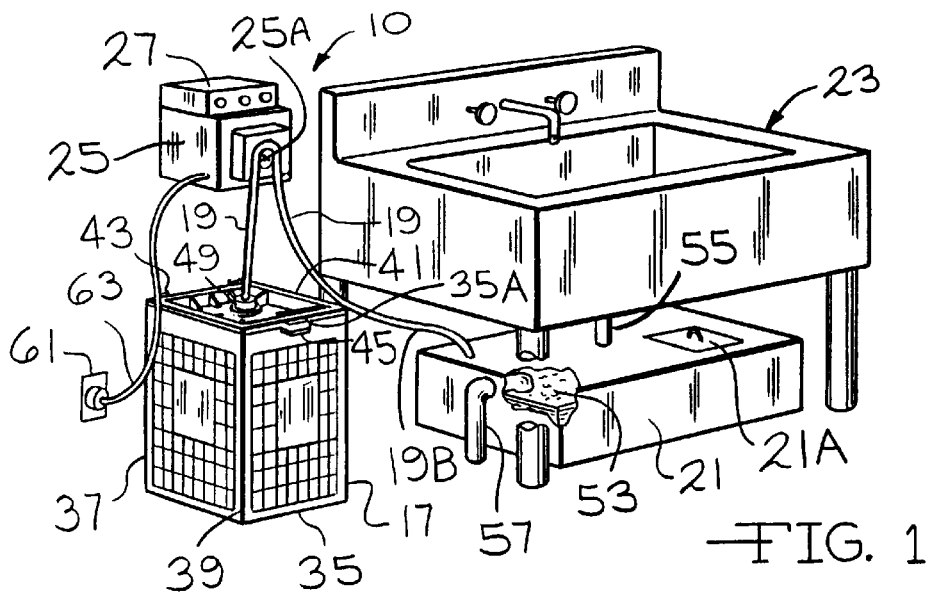
FIG. 1
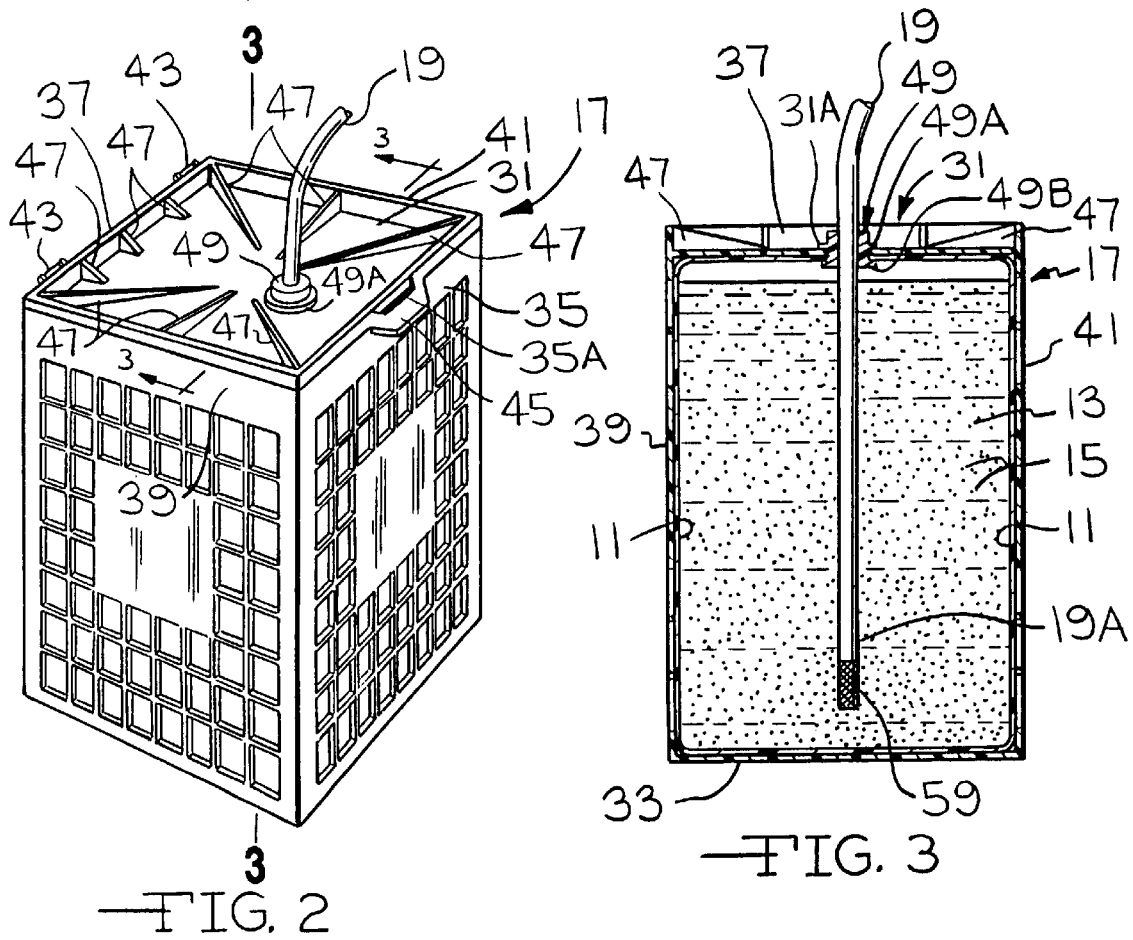
FIG. 2
FIG. 3

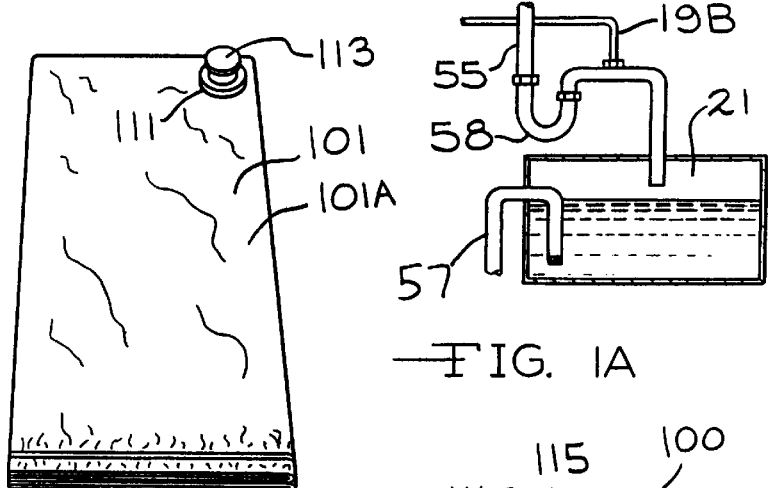
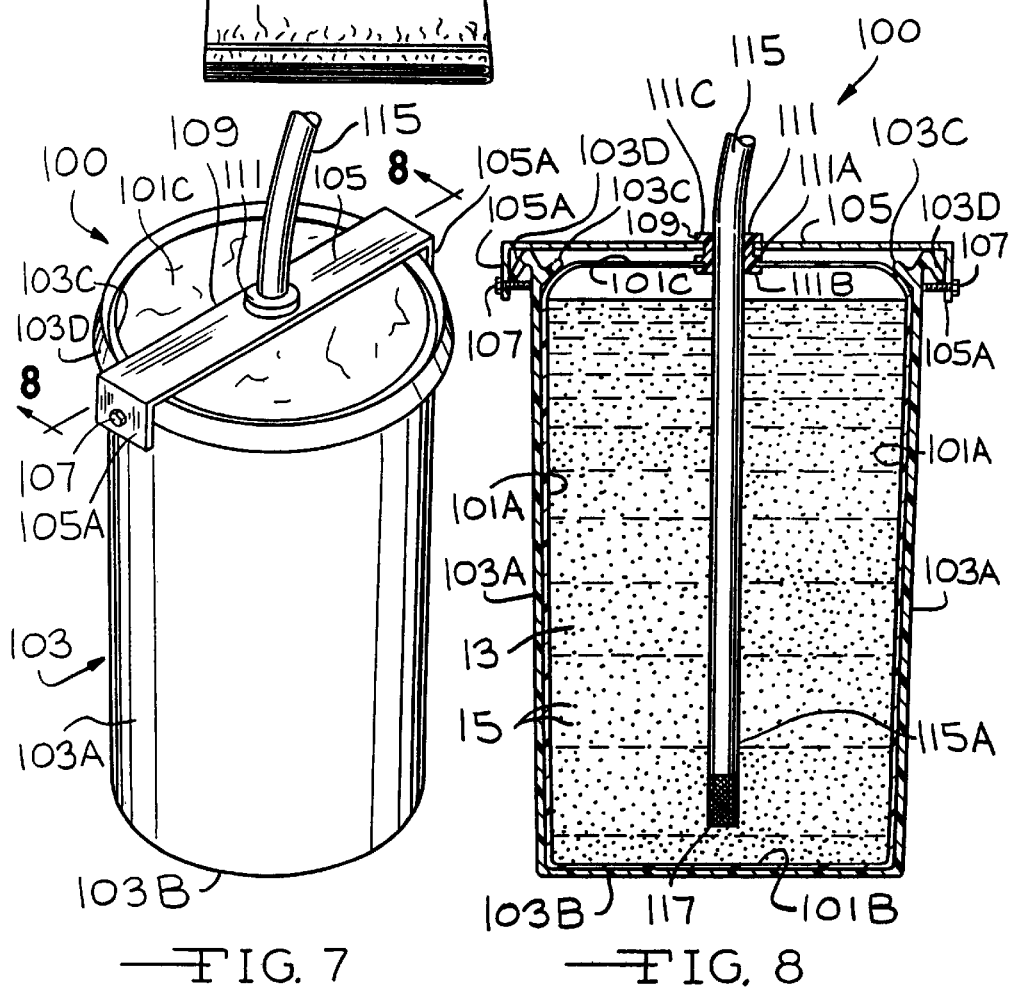

METHOD AND APPARATUS FOR WASTE DEGRADATION

BACKGROUND OF THE INVENTION (1) Field of the Invention

The present invention relates to an apparatus and a method for introducing waste degrading microorganisms into a waste system for degrading hydrocarbon waste compositions into carbon dioxide and water. In particular, the present invention relates to an apparatus and a method for degrading a liquid waste composition containing lipids, aromatic, aliphatic and other organic compounds by introducing hydrocarbon degrading microorganisms into a system containing the waste compositions. The microorganisms feed on the waste hydrocarbons to render the resulting solution non-polluting. The degraded solution is then removed by the sewage system without posing a risk to the environment.

(2) Prior Art

Organic compounds have been shown to be degraded as described in the following references: U.S. Pat. No. 4,452,894 to Olsen et al; U.S. Pat. No. 4,593,003 to Vandenbergh; Vandenbergh, P. A. and A. M. Wright, Appl. Environ. Microbiol. 45: 1953–1955 (1983); Vandenbergh, P. A., C. F. Gonzalez, A. M. Wright and B. S. Kunka, Appl. Environ. Microbiol. 46: 128–132 (1983); Vandenbergh, P. A., R. H. Olsen and J. F. Colaruotolo, Appl. Environ. Microbiol. 42: 737–739 (1981); and Vandenbergh, P. A., and R. L. Cole, Appl. Environ. Microbiol. 52: 939–940 (1986). The useful application of bacteria to the environment to degrade waste has been previously demonstrated by U.S. Pat. No. 4,593,003 to Vandenbergh. Also, U.S. Pat. No. 4,910,143 to Vandenbergh describes a mixture of *Pseudomonas putida* strains for degrading waste chemical compositions of the kind that are commonly found in the environment.

However, what is needed is an inexpensive and reliable apparatus that is useful for dispensing microorganisms for degrading wastes that are typically generated as a by-product of food preparation, such as is usually found in restaurants and the like. These wastes are typically fats and oils. Wastes that are generated during the preparation of foods are periodically removed for treatment. The former practice poses serious pollution problems for the environment and is not acceptable. As a practical matter, it is not possible to remove all of the waste which accumulate and some go down the drain. Most food preparation facilities have a trap which retains such wastes. The present invention provides a means for disposing of the wastes in such traps.

There is also a need for an apparatus for dispensing microorganisms in an industrial setting. There is also a need for an inexpensive and reliable apparatus in this use setting.

OBJECTS

It is therefore an object of the present invention to provide an apparatus for dispersing microorganisms into a waste material for degrading the waste. Further, it is an object of the present invention to provide a method for degrading a waste material held in a containment vessel or trap with a solution of microorganisms wherein the waste containment vessel is periodically reinoculated with a fresh supply of the solution to ensure the continued degradation of the waste material. Further still, it is an object of the present invention to provide an apparatus for degrading a waste material that is easy to set up and operate, and that can be retrofitted to existing waste storage vessels such as in restaurant kitchens and in industrial plants. These and other objects will become increasingly apparent by reference to the following description and to the drawings.

IN THE DRAWINGS

FIG. 1 is a perspective view of a waste degradation system 10 showing a crate 17 containing a bag 11 of microorganisms or cells 15 in an aqueous solution 13 with a peristaltic pump 25 controlled by a timer 27 for pumping the solution 13 into a waste trap 21 containing liquid waste material 53.

FIG. 1A is a schematic view of a discharge end 19B of the feed line 19 of the waste degradation system 10 as shown in FIG. 1 connected to the drain line 55 after the drain line trap 58.

FIG. 2 is a perspective view of the crate 17 for holding the bag 11 of microorganisms 15 of the waste degradation system of FIG. 1 showing a solution feed line 19 entering the bag 11 through a plug 49.

FIG. 3 is a cross-sectional view along line 3—3 of FIG. 2 showing the feed line 19 for drawing the aqueous solution 13 of microorganisms 15 from the bag 11 supported by the crate 17.

FIG. 4 is a perspective view of a plurality of bags 11 containing the microorganisms 15 for the waste degradation system of FIG. 1 packaged in a carton 29 for shipping.

Figure 5:
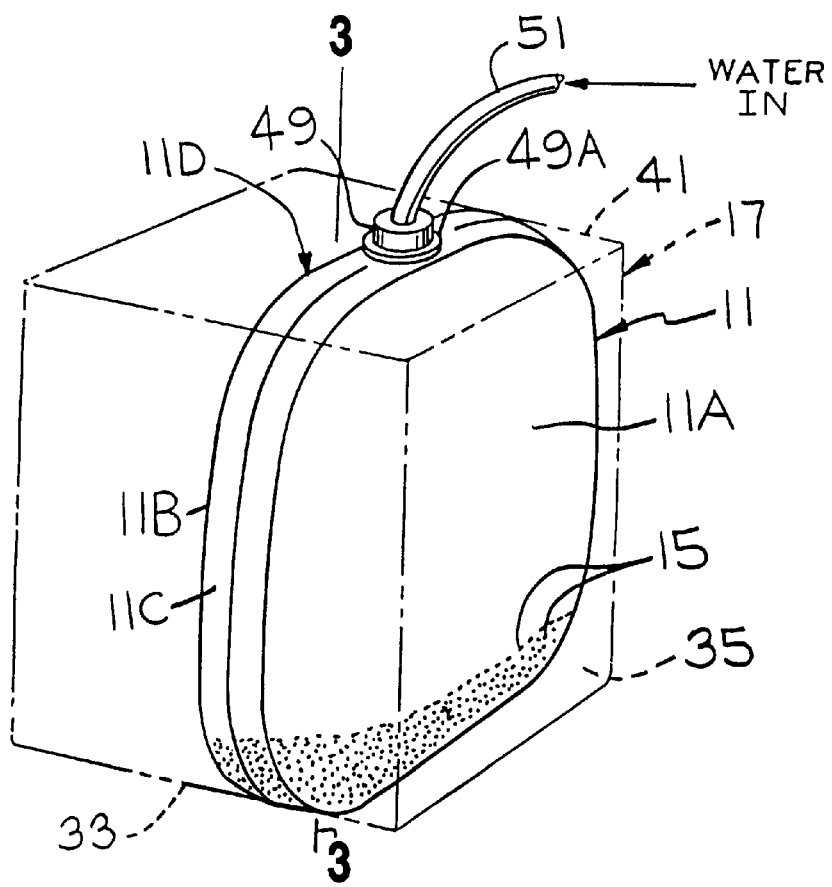

FIG. 5 is a perspective view of the bag 11 of the waste degradation system of FIG. 1 supported in the crate 17 for filling the bag 11 with water through hose 51 to bring the microorganisms 15 into solution 13, with the crate 17 shown in dashed lines.

FIG. 6 is a schematic view of a bag 101 containing the microorganisms 15 for a waste degradation system 100 particularly adapted for industrial use.

FIG. 7 is a perspective view of the waste degradation system 100 with the bag 101 mounted in a drum 103.

FIG. 8 is a cross-sectional view along line 8—8 of FIG. 7 showing the feed line 117 for drawing the aqueous solution 13 of microorganisms 15 from the bag 101 supported by the drum 103.

GENERAL DESCRIPTION

The present invention relates to a method for treating a waste material to degrade the waste material, which comprises: providing a containment means for holding microorganisms that can degrade the waste material; filling the containment means with water to form a liquid culture medium with the microorganisms, and metering the liquid culture medium into the waste material over time to degrade the waste material, wherein the liquid culture medium is maintained at ambient temperatures during the metering.

Further, the present invention relates to a method for treating liquid waste material to degrade the waste, which comprises: providing a collapsed, flexible bag with a closable and sealable opening and containing microorganisms which can degrade the waste material, wherein microorganisms contained in the bag are held at reduced temperatures so that the microorganisms are viable prior to use; expanding and completely filling the bag with water through the opening, wherein the bag is provided in a containment means, which supports the bag to form a liquid culture medium with the microorganisms; and metering the liquid culture medium into the waste material over time to degrade the waste material, wherein the liquid culture medium is maintained at ambient temperatures during the metering.

Further, the present invention relates to a method for treating a drain to degrade lipids which tend to clog the drain, which comprises: providing a collapsed, flexible bag means with a closable and sealable opening and containing microorganisms, which degrade the lipids wherein the collapsed bag means is held at reduced temperatures so that the microorganisms are viable to process viability prior to use; expanding and completely filling the bag means with water through the opening in the bag means to form a liquid culture medium containing the microorganisms, wherein the bag means is provided in a containment means, which supports the bag means; and metering the liquid culture medium through the opening in the bag means and into a drain over time to degrade the lipids in the drain, wherein the liquid culture medium is maintained at ambient temperatures during the metering.

Still further, the present invention relates to an apparatus for metering microorganisms into a waste stream which comprises: a collapsible flexible bag means with a closable and sealable opening, a bottom at a lower end and flexible sidewalls between the ends for containing the microorganisms when collapsed and providing a liquid culture medium when the bag means is filled with water for metering into the waste system; a containment means for supporting the sidewalls and bottom of the flexible bag means when filled with the liquid culture medium and with an open top into which the bag means has been inserted; a first, flexible conduit means mounted through the closable opening in the bag means, to adjacent the bottom of the bag means and extending from the bag means through which the liquid culture medium can flow; a pump means for metering the liquid culture medium through the first conduit means and into the waste stream; and a second, flexible conduit means leading from the pump to the waste stream.

Finally, the present invention relates to an apparatus for metering microorganisms into a drain, which comprises: a flexible bag means with a closable and sealable opening and a bottom at a lower end and flexible sidewalls for containing the microorganisms when collapsed and providing a liquid culture medium when the bag means is filled with water for metering into the drain; a box shaped containing means for supporting the sidewalls and the bottom of the flexible bag means when filled with the liquid culture medium and with an open top into which the bag has been inserted; a first flexible conduit means connected through the closable opening in the bag means, to adjacent the bottom of the bag means and extending from the bag means; a pump means for mounting on a wall adjacent to the drain for metering the liquid culture medium into the drain; and a second flexible conduit means leading from the pump means to the drain.

The microorganisms used are preferably Pseudomonas and Bacillus; however, other bacteria and fungi are also known to degrade waste. Such microorganisms are well known to those skilled in the art.

The microorganisms can be cultured in various growth mediums. The microorganisms can usually be grown in a growth medium containing yeast extract, dextrose, tryptone, potassium nitrate and sodium chloride. The yeast extract provides nitrogen and vitamins. Dextrose is a carbon source. The inorganic salts aid growth. Normally bacterial strains only grow to about $10^9$ cells per gram and can be concentrated to $10^{14}$ cells per gram. The cells are preferably centrifuged from the growth medium to provide a concentrate containing between about $10^{11}$ and $10^{12}$ cells per gram. The microbial cells are preferably freeze-dried or lyophilized as is well known to those skilled in the art. Other methods involving air drying the cells is also known and the cells can be held at room temperatures. The microbes can also be held as a culture at reduced temperatures without being dried.

Specific Description

EXAMPLE 1

FIGS. 1 to 5 illustrate one preferred embodiment of a waste degradation system 10 of the present invention. The system 10 includes a bag 11 as a container for holding an aqueous solution 13 of microorganisms 15 supported in a crate 17 for the bag 11. A solution feed hose 19 connects between the bag 11 and a waste trap 21 for a sink 23. A pump 25 having a timer 27 regulates the periodic flow of the microorganism solution 13 from the bag 11, through the hose 19 and into the waste trap 21.

The microorganisms 15 are grown in a growth medium as explained above and centrifuged, membrane filtered and/or otherwise concentrated to a concentration of between about $10^{11}$ and $10^{12}$ cells per gram. The microorganisms 15 are then preferably freeze-dried or lyophilized and held at reduced temperatures, preferably between about 32° F. and 59° F. (0° C. and 15° C.) (refrigeration temperatures) to preserve the microorganisms 15 viability prior to use.

The process of freeze-drying or lyophilizing the microorganisms 15 can be extremely damaging to the microorganisms 15. Typically, between 60% to 70% of the microorganisms 15 perish during the lyophilizing process. However, as explained above, the concentration of microorganisms 15 is large enough before the lyophilizing process that a significant number survive the lyophilizing process. The concentration of microorganisms 15 that survive the lyophilizing or freeze-drying process is between about $4\times10^{10}$ and $4\times10^{13}$ cells per gram. This concentration is sufficient for use in the waste degradation system 10. The microorganisms 15 can also be preserved by air drying, using certain preservatives. The air dried process takes place at elevated temperatures which maintain the viability of the microorganisms 15. The air drying process is known to those skilled in the art.

After the microorganisms 15 have been concentrated and preserved, the microorganisms 15 are placed in the bags 11 for later shipment. The dried microorganisms 15 can be stabilized to provide a longer life when water is added by using starch, sodium nitrate or other stabilizing agent. The amount of the stabilizing agent is 2 ounces (56.7 grams) per 5 gallons (18.9 liters), or 20 ounces (566.6 grams) per 50 gallons (189.4 liters). The range is preferably 0.1 to 5 ounces (2.8 to 141.6 grams) per 5 gallons (18.9 liters).

As shown in FIG. 4, the bags 11 are folded to minimize space and packaged in a shipping carton 29. There are preferably twenty (20) bags 11 per carton 29. If the microorganisms 15 are lyophilized, it is important that the carton 29 containing the bags 11 be stored in a freezer before use to maintain the microorganisms 15 in a viable state. Refrigerating the carton 29 can be done by any acceptable means. Preferably, the carton 29 is packed in dry ice or is shipped in a refrigerated shipping container (not shown). Microorganisms 15 preserved by air drying can be held at room temperatures.

The microorganisms 15 can be light sensitive and thus die faster when exposed to light. Therefore, the bags 11 are preferably made of a flexible, plastic material such as polypropylene, which is opaque or translucent to reduce the amount of light reaching the microorganisms 15.

To prepare the microorganisms 15 for use in a restaurant, a bag 11 containing the microorganisms 15 is first placed in the crate 17, as shown in dashed lines in FIG. 5. The crate 17 has a rectangular cross-section along a longitudinal axis A—A (FIGS. 2 and 5) and includes a top wall 31, a bottom end 33, a front side 35, a back side 37 and opposed lateral sides 39 and 41 between the front and back sides 35 and 37. The front side 35, the back side 37 and the opposed lateral sides 39 and 41 have a generally rectangular mesh that enables a person to visually see the bag 11 through the crate 17.

As shown in FIG. 2, the top wall 31 of the crate 17 is hinged to the back side 41 by hinges 43. When the top wall 31 is in the closed position (FIGS. 2 and 3), a front latch 45 mates with a catch 35A on the front side 35 of the crate 17. An opening 31A (FIG. 3), is provided in the top wall 31 for receiving the bag 11. The opening 31A is offset from the axis A—A when the top wall 31 is in the closed position. Braces 47 add support to the top wall 31 to help the top wall 31 support the weight of the filled bag 11.

As shown in FIGS. 3 and 5, the bag 11 is comprised of opposed front and back walls 11A and 11B joined by a sidewall 11C that extends between the perimeter of the side walls 11A and 11B. A filler plug 49 having spaced apart upper and lower annular rims 49A and 49B is mounted in the top of the sidewall 11C of the bag 11. The filler plug 49 is preferably made of an elastic material so that the upper annular rim 49A mounts in the opening 31A in the top 31 of the crate 17. This keeps the bag 11 suspended in the crate 17 while the bag 11 is being filled with water (FIG. 5) to form the aqueous solution 13 of the microorganisms 15 and later, as the solution 13 is being drained from the bag 11.

As shown in FIG. 5, the aqueous solution 13 of the microorganisms 15 is made by first suspending the bag 11 in the crate 17 with the filler plug 49 mounted in the opening 31A in the top wall 31. A filler hose 51 is then inserted into the filler plug 49 to fill the bag 11 with water until the bag 11 expends to the confines of the inside of the crate 17. The water brings the microorganisms 15 to ambient temperature, which activates the microorganisms 15 from their lyophilized or air-dried state. The water is preferably held at a temperature of between about 59° F. and 95° F. (15° C. and 35° C.). The bag 11 held in the crate 17 is preferably capable of holding about 5 gallons (18.9 liters) of the aqueous solution 13 of microorganisms 15, which lasts about two (2) to four (4) weeks, primarily because of the need to maintain the viability of the microorganisms 15 at room temperatures. The solution 13 can last up to 30 days depending upon what stabilizing agent is used.

As shown in FIG. 1, the crate 17 supporting the bag 11 containing the microorganisms 15 in solution 13 along with the feed line 19, the peristaltic pump 25 and the timer 27 comprise the waste degradation system 10. The microorganisms 15 are particularly adapted to biodegrade liquid waste material 53 containing lipids or other hydrocarbons of the type that are typically discharged into the waste trap 21 such as is found in a restaurant or the like. Generated liquid waste 53 is usually placed in the sink 23 and flushed down the drain line 55 where the waste 53 collects in the waste trap 21. Therefore, to biodegrade the waste 53 so that the resulting solution can be drawn out of the waste trap 21 by a discharge line 57 and moved to a sewer system (not shown) without posing a pollution risk to the environment, the solution 13 is periodically metered into the waste trap 21 containing the liquid waste material 53. As shown in FIG. 1A, the solution 13 can also be metered into the drain line 55 leading to the waste trap 21. In this case, it is preferred that the discharge end 19B of the feed line 19 connect with the drain line 55 downstream from the drain line trap 58. The feed line 19 can also connect with the drain line 55 upstream from the drain line trap 58, although this is not preferred. In the waste trap 21, the microorganisms 15 feed on the liquid waste 53, rendering the waste 53 free of lipids and other harmful hydrocarbons.

Before the metering process begins, it is preferred that the waste trap 21 be inoculated with an initial charge of the microorganisms 15. This is done by opening the trap lid 21A on the waste trap 21 and pouring a relatively large dosage of the microorganisms 15 into the waste trap 21. The liquid waste material 53 with the initial charge of microorganisms 15 is then agitated with a hoe or similar device. The initial charge of microorganisms 15 is preferably between about seven (7) ounces (200 grams) of a mixed Pseudomonas culture containing $1 \times 10^{12}$ cells per gram. The purpose of introducing the initial charge of microorganisms 15 into the waste trap 21 is to make sure that the initial liquid waste 53 present in the waste trap 21 is rendered free of lipids and other harmful hydrocarbons before the metering process of the solution 13 into the waste trap 21 begins. The culture is available from Osprey Biotechnics, Inc., Oneco, Fla. as "ST". The culture for the solution is Munox GT™.

The metering process is done at predetermined intervals or time periods to ensure that the waste material 53 in the waste trap 21 is continuously charged with a solution 13 of the microorganisms 15 in a concentration that is sufficient to degrade the liquid waste 53. The feed line 19 is preferably a flexible conduit made of a plastic material and connects to the peristaltic pump 25, which serves to move the microorganism solution 13 from the bag 11 to the waste trap 21. A lower end 19A of the feed line 19 can be provided with a strainer 59 to prevent obstruction of the feed line 19 by the bag 11. This would likely occur as the solution 13 is being depleted from the bag 11 and the bag 11 begins to collapse around the feed line 19. The peristaltic pump 25 is provided with electrical power from electrical outlet 61 by electrical lead 63 and has a rotating member 25A that forces the microorganism solution 13 from the bag 11, through the feed line 19 and into the waste trap 21. In this manner, the microorganisms 15 are not injured by the pumping action of pump 25. An integral timer 27, mounted on the pump 25, serves to actuate the pump 25 at predetermined time intervals. The pump 25 is preferably actuated for about 15 minute intervals, six times every 24 hours or every six seconds to provide a preferred dosage of 0.74 to 1.48 quarts (700 to 1400 ml) every 24 hours for the 5 gallon (18.9 liters) bag 11. This ensures that the waste trap 21 is periodically reinoculated with the microorganism solution 13 should the drain line 55 leading from the sink 23 into the waste trap 21 become flooded with chlorine or boiling water or any other solution that is toxic to the microorganisms 15.

Carton 29, holding twenty (20) folded bags 11 of the freeze-dried or lyophilized microorganisms 15 is shipped to an end user in a refrigerated state. When the user wants to rid the waste trap 21 of liquid waste material 53 containing lipids and other hydrocarbons, the user removes a single bag 11 from the carton 29 and mounts the bag 11 in the crate 17. The bag 11 is then mounted in the crate 17. This is done by mounting the upper annular rim 49A of the filler plug 49 in the opening 31A of the top wall 31 of the crate 17. The top wall 31 is then closed on the crate 17 with the front latch 45 mating with the catch 35A on the front side 35 of the crate 17.

The filler hose 51 is then inserted into the filler plug 49 (FIG. 5) and the bag 11 is filled with water to make the aqueous solution 13 containing the microorganisms 15. The water is preferably at about 72° F. (22° C.) and the solution

13 contains microorganisms 15 at a concentration of about $10^6$ cells per gram of solution 13. As the bag 11 is being filled with water, the crate 17 serves to support the bag 11 to keep the bag 11 from rupturing or collapsing.

Once the bag 11 is filled with water, the filler hose 51 is removed from the bag 11 and the feed hose 19 is inserted into the filler plug 49 in place of the filler hose 51. The strainer 59 at the lower end 19A of the feed hose 19 is positioned off the bottom end 33 of the crate 17. The feed line 19 is positioned on the rotor 25A of the peristaltic pump 25 (FIG. 1) and the discharge end 19B of the feed line 19 is placed in the waste trap 21. The peristaltic pump 25 is preferably actuated for 15 minute intervals, six times in a 24 hour period, or every six seconds, to move the solution 13 from the bag 11 to the waste trap 21. That way, the waste trap 21 is periodically reinoculated with a fresh charge of the solution 13.

EXAMPLE 2

FIGS. 6 to 8, illustrate another preferred embodiment of a waste degradation system 100 of the present invention. This embodiment is particularly adapted to use the microorganisms 15 to biodegrade hydrocarbon waste in an industrial setting. As shown in FIG. 6, the system 100 includes a bag 101 that contains the microorganisms 15 in a lyophilized or air-dried state. The bag 101 is preferably made of a flexible, plastic material such as polypropylene, which is opaque or translucent to reduce the amount of light reaching the microorganisms 15. After the microorganisms 15 are placed in the bag 101, the bag 101 is folded and packaged for later shipment to an end user. If the microorganisms 15 have been lyophilized or freeze-dried, the bag 101 is then kept in a refrigerated condition until use, as has been previously explained. It is also preferred that the microorganisms 15 be provided with a stabilizing agent, as has been previously explained.

To prepare the microorganisms 15 for use in an industrial setting, a bag 101 containing the microorganisms 15 is placed in a drum 103. The drum 103 preferably holds about 55 gallons (208.3 liters) of solution 13 containing the microorganisms 15 and is comprised of a cylindrical sidewall 103A extending from a bottom wall 103B. An upper end of the sidewall 103A of the drum 103, has an inwardly extending annular ledge 103C and an outwardly and downwardly extending annular rim 103D. An elongate bar 105, having spaced apart downwardly extending ends 105A, is mounted diametrically across the top of the drum 103. The ends 105A of bar 105 extend below the annular rim 103D of drum 103 and provide for threadably mounting bolts or screws 107. The bolts 107 can be unthreaded to a loosened position (not shown) for removing the bar 105 from the drum 103. The bar 105 is also provided with a central opening 109 that provides for mounting the bag 101.

As shown in FIG. 8, the bag 101 is comprised of a cylindrical sidewall 101A extending from a bottom wall 101B to a top wall 101C. The top wall 101C of the bag 101 is provided with a filler plug 111 having a stopper 113 when the bag 101 is being shipped and before use in the drum 103. The filler plug 111 has spaced apart upper and lower annular rims 111A and 111B, which seal the filler plug 111 in the top wall 101C of the bag 101. The filler plug 111 is preferably made of an elastic material and has an annular lip 111C that provides for mounting the plug 111 in the opening 109 in the bar 105. This keeps the bag 101 suspended in the drum 103 while the bag is being filled with water to form the aqueous solution 13 of microorganisms 15 and later, as the bag 101 is being drained of the solution 13. The bar 105 is then secured to the top of the drum 103 with the bolts 107 threaded to engage the sidewall 103A of the drum 103.

As has been previously described, the aqueous solution 13 of microorganisms 15, is made by filling the bag 101, which has been mounted to the bar 105 and suspended in the drum 103, with water until the bag 101 expands to the confines of the inside of the drum 103. The water brings the microorganisms 15 to ambient temperature, which activates the microorganisms 15 from their lyophilized or air-dried state. The water is preferably held at a temperature of between about 59° F. and 95° F. (15° C. and 35° C.) and the bag 101, held in the drum 103 is preferably capable of holding about 55 gallons (208.3 liters) of the aqueous solution 13. This amount of solution 13 preferably lasts about two (2) to four (4) weeks, although the solution 13 can be dispersed over the period of one (1) day.

In use, the bag 101 is provided with a feed line 115 as a flexible conduit means of a plastic material that connects to a peristaltic pump (not shown) controlled by a timer (not shown) in a similar manner as previously described with respect to the restaurant system of Example 1. A lower end 115A of the feed line 115 can be provided with a strainer 117 to prevent obstruction of the feed line 115 by the bag 101 as the solution 13 is depleted from the bag 101 and the bag 101 begins to collapse around the feed line 115. The peristaltic pump is preferably actuated for 15 minute intervals, six times in a 24 hour period, or every six seconds, as discussed above to move the solution 13 from the bag 101 to an industrial waste trap (not shown). This provides a preferred dosage of 8.1 to 16.3 quarts (7,700 to 15,400 ml) every 24 hours for the 55 gallon (208.3 liters) bag 101. That way, the waste trap is periodically reinoculated with a fresh charge of the solution 13 to biodegrade liquid waste material containing lipids or other hydrocarbons that have been discharged into the waste trap.

As explained with respect to Example 1, the industrial waste trap is initially inoculated with an initial charge of culture. Once the industrial waste trap is charged with the culture, the waste trap is periodically reinoculated with the solution 13 to biodegrade the liquid waste material in the waste trap.

It has been unexpectedly found that the present invention prevents plugging of the drain lines in both restaurant and industrial settings because fats and the like, which cling to the wall of the drain lines, are dissolved. This is of considerable aid to the municipalities.

It is intended that the foregoing description be only illustrative of the present invention and that the present invention be limited only by the hereinafter appended claims.

I claim:

1. A method for treating a waste material to degrade the waste material, which comprises:

(a) providing a flexible bag containing concentrated microorganisms which are dried with between about $4\times10^{10}$ and $10^{14}$ living cells of the microorganism per gram that can degrade the waste material for storage and shipment of the microorganisms in the bag prior to use;

(b) filling the bag of step (a) with water to form a liquid culture medium with the microorganisms at a place remote from the shipment and inoculating the waste with an initial charge of the concentrated microorganisms with between about $4\times10^{10}$ and $10^{14}$ living cells of the microorganism per gram; and (c) metering the liquid culture medium containing the microorganisms from the bag using a feed line leading from the bag through a pump means and from the pump means without connection to any other feed line to supply the culture medium containing the microorganisms at periodic intervals over 24 hours, into the waste material containing the microorganisms over time to degrade the waste material, wherein the liquid culture medium is maintained at ambient temperatures during the metering.

2. The method of claim 1 wherein the microorganisms are naturally occurring soil microorganisms selected from a group consisting of Pseudomonas and Bacillus.

3. The method of claim 1 wherein the bag is collapsed and provided with a closable and sealable filler opening through the bag and wherein the bag is mounted in a support means with the bag expanded and filled with water through the filler opening in the bag to form the liquid culture medium and wherein the support means helps to support the bag containing the liquid culture medium.

4. The method of claim 3 wherein the support means is a crate and after the bag is expanded and filled with water to form the liquid culture medium, the bag holds about 5 gallons of the liquid culture medium in the crate and wherein to degrade waste material from a restaurant, the liquid culture medium is metered into a waste confining means holding the waste material inoculated with the microorganisms to degrade the waste material produced by the restaurant.

5. The method of claim 3 wherein the support means is a drum and after the bag is expanded and filled with water to form the liquid culture medium, the bag holds about 55 gallons of the liquid culture medium supported by the drum and wherein to degrade waste material from an industrial setting, the liquid culture medium is metered into a waste confining means holding the waste material containing the microorganisms to degrade the waste material produced in the industrial setting.

6. The method of claim 1 wherein the pump means is a peristaltic pump.

7. The method of claim 6 wherein timing control means connected to the pump means is provided for metering the liquid culture medium into a drain containing the waste material at the periodic intervals.

8. The method of claim 7 wherein the liquid culture medium contains at least about $10^6$ cells per gram.

9. The method of claim 8 wherein the support means is a crate and after the bag is expanded and filled with water to form the liquid culture medium, the bag holds about 5 gallons of the liquid culture medium in the crate and wherein to degrade waste material from a restaurant, the liquid culture medium is metered into a waste confining means holding the waste material containing the microorganisms to degrade the waste material produced by the restaurant.

10. The method of claim 9 wherein every 24 hours, the pump means meters between about 700 and 1,400 ml of the liquid culture medium into the waste confining means to degrade the waste material over a period of up to 30 days.

11. The method of claim 8 wherein the support means is a drum and after the bag is expanded and filled with water to form the liquid culture medium, the bag holds about 55 gallons of the liquid culture medium supported by the drum and wherein to degrade waste material from an industrial setting, the liquid culture medium is metered into a waste confining means holding the waste material containing the microorganisms to degrade the waste material produced in the industrial setting.

12. The method of claim 11 wherein every 24 hours, the pump means meters between about 7,700 and 15,400 ml of the liquid culture medium into the waste confining means to degrade the waste material over a period of up to 1 day.

13. A method for treating a liquid waste material to degrade the waste, which comprises:

(a) providing a collapsed, flexible bag with a closable and sealable filler opening and containing concentrated microorganisms which can degrade the waste material, wherein the concentrated microorganisms which are dried with between about $4\times10^{10}$ and $10^{14}$ living cells of the microorganism per gram and which are contained in the bag so that the microorganisms are viable for storage and shipment of the microorganisms in the bag of step (a) prior to use;

(b) expanding and completely filling the bag at a place remote from the shipment with water through the filler opening, wherein the bag is provided in a support means, which supports the bag to form a liquid culture medium with the microorganisms with the filler opening at an uppermost portion of the bag and inoculating the waste with an initial charge of the concentrated microorganisms with between about $4\times10^{10}$ and $10^{14}$ living cells of the microorganism per gram; and (c) metering the liquid culture medium from the bag using a feed line leading from the bag through a pump means and from the pump means without connection to any other feed line to supply the culture medium at intervals over 24 hours, through the filler opening into the waste material containing the microorganisms to degrade the waste material, wherein the liquid culture medium is maintained at ambient temperatures during the metering.

14. The method of claim 13 wherein the microorganisms are naturally occurring soil Pseudomonas.

15. The method of claim 13 wherein the bag is made of blow molded polypropylene.

16. The method of claim 13 wherein the liquid culture medium is metered into the waste material over a period of about 1 to 3 days to degrade the waste material.

17. A method for treating a drain line to degrade lipids which tend to clog the drain line, which comprises:

(a) providing a collapsed, flexible bag with a closable and sealable filler opening and containing concentrated microorganisms which are dried with between about $4\times10^{10}$ and $10^{14}$ living cells of the microorganism per gram, which degrade the lipids, wherein the collapsed bag is comprised of a plastic which reduces light reaching the microorganisms through the bag and is held at reduced temperatures so that the concentrated microorganisms are viable during storage and shipment of the microorganisms in the bag prior to use;

(b) expanding and completely filling the bag of step (a) with water through the opening in the bag to form a liquid culture medium containing the microorganisms at a place remote from the shipment, wherein the bag is provided in a support means, which supports the bag with the filler opening at an uppermost portion of the bag and inoculating the waste with an initial charge of the concentrated microorganisms with between about $4\times10^{10}$ and $10^{14}$ living cells of the microorganism per gram; and (c) metering the liquid culture medium through the filler opening in the bag using a feed line through the filler opening in the bag through a pump means and from the pump means without connection to any other feed line to supply the culture medium containing the microorganisms, and into a drain line over time to degrade the lipids in the drain line, wherein the liquid culture medium is maintained at ambient temperatures during the metering and wherein the bag collapses as the liquid culture medium is withdrawn through the feed line.

18. The method of claim 17 wherein the containment means is a crate with an open top into which the bag is inserted prior to filling with water so that the baa rests inside the crate.

19. The method of claim 18 wherein after the bag is expanded and filled with water to form the liquid culture medium, the bag holds about 5 gallons of the liquid culture medium and is supported in the crate.

20. The method of claim 17 wherein the support means is a drum and after the bag is expanded and filled with water to form the liquid culture medium, the bag holds about 55 gallons of the liquid culture medium and is supported in the drum.

21. The method of claim 17 wherein the metering is into a sink line leading from a sink trap.

22. The method of claim 17 wherein the microorganisms are naturally occurring soil microorganisms selected from a group consisting of Pseudomonas and Bacillus.

23. The method of claim 17 wherein the feed line at an end inside the bag is provided with a strainer to prevent obstruction of the feed line by the bag as the bag is emptied of the liquid culture medium.

* * * * *

UNITED STATES PATENT AND TRADEMARK OFFICE
CERTIFICATE OF CORRECTION

PATENT NO. : 5,935,843
DATED : August 10, 1999
INVENTOR(S) : Larrick H. Glendening and Vincent J. Scuilla It is certified that error appears in the above—identified patent and that said Letters Patent is hereby corrected as shown below:

Column 11, line 12 (Claim 18), "baa" should be --bag--.

Signed and Sealed this

Eighth Day of February, 2000

Attest:

Q. TODD DICKINSON

Attesting Officer

Commissioner of Patents and Trademarks